United States Patent [19]

Ngo et al.

[11] Patent Number: 5,328,834
[45] Date of Patent: Jul. 12, 1994

[54] METHOD FOR PREPARING IMMUNOGLOBULIN FRAGMENTS

[75] Inventors: That T. Ngo, Irvine; Harish P. M. Kumar, El Toro, both of Calif.

[73] Assignee: UniSyn Technologies, Inc., Tustin, Calif.

[21] Appl. No.: 404,992

[22] Filed: Sep. 8, 1989

[51] Int. Cl.$^5$ .............................................. C12P 21/00
[52] U.S. Cl. .................................. 435/68.1; 530/387.1
[58] Field of Search ............. 435/68.1; 530/388, 387.1

[56] References Cited

U.S. PATENT DOCUMENTS

| | | | |
|---|---|---|---|
| 4,436,724 | 3/1984 | Ohimski et al. | 435/68.1 |
| 4,719,107 | 1/1988 | Carosella et al. | 424/85.8 |
| 4,742,159 | 5/1988 | Batz et al. | 435/68.1 |
| 4,806,346 | 2/1989 | Hum et al. | 435/68.1 |
| 4,814,433 | 3/1989 | Fredrickson | 435/68.1 |
| 4,849,352 | 7/1989 | Sullivan et al. | 435/68.1 |
| 4,874,708 | 10/1989 | Makula et al. | 435/68.1 |
| 4,886,758 | 12/1989 | Eibl et al. | 435/68.1 |

*Primary Examiner*—Allen J. Robinson
*Assistant Examiner*—Shailendra Kumar
*Attorney, Agent, or Firm*—Edward S. Irons

[57] ABSTRACT

A method for preparation of immunoglobulin fragments by specific fragmentation of immunoglobulins, comprising treating a solution of immunoglobulins with a soluble protease so as to achieve substantially complete fragmentation of the immunoglobulins, followed by complexing the protease with a complexing agent (for example, antibody to the protease) to form a protease complex and separating the protease complex from the immunoglobulin fragments. Optionally, the protease (e.g., pepsin or papain) is inactivated prior to formation of the protease complex. In contrast to methods which use immobilized forms of the enzymes, the rate of cleavage and the final yields of $F_{(ab)}$ and $F_{(ab')2}$ fragments are increased substantially.

11 Claims, 4 Drawing Sheets

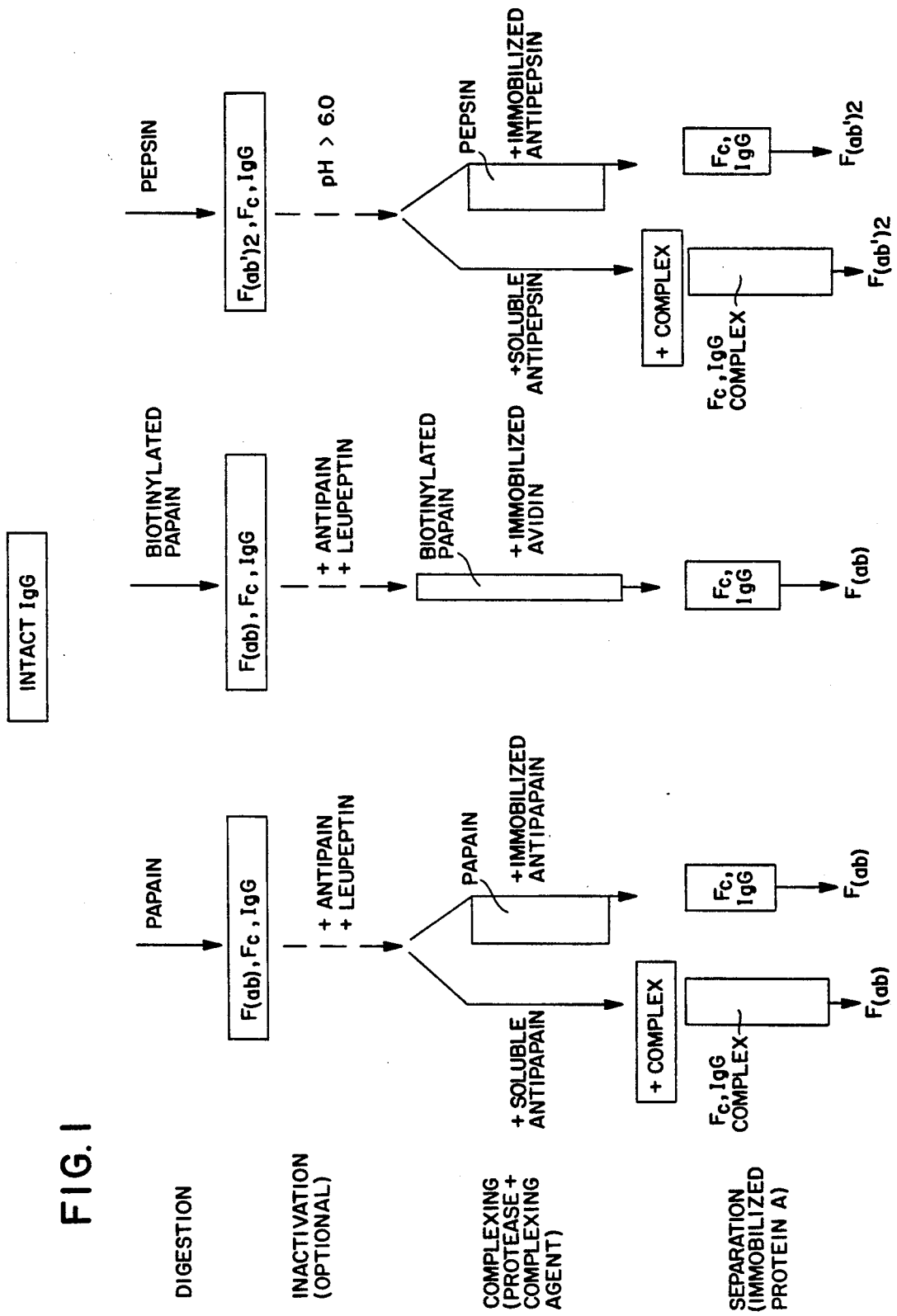

1 2 3 4 5 6 7

6 5 4 3 2 1

METHOD FOR PREPARING IMMUNOGLOBULIN FRAGMENTS

BACKGROUND OF THE INVENTION

This invention relates to methods for preparing and isolating fragments of immunoglobulins from the whole proteins in a rapid and highly efficient manner.

Proteolytic digestion of immunoglobulin molecules have been used for some time to investigate the immunological and other biological properties of antibodies and fragments thereof. Papain and pepsin are the most commonly used proteases to generate $F_{(ab)}$ and $F_{(ab')2}$ fragments, respectively. Both of these fragments retain some immunological reactivity, although only the $F_{(ab')2}$ fragment further retains the ability to form precipitable antigen-antibody complexes. The original work of Porter used soluble forms of papain and pepsin; the fragmented antibody and the protease were separated after proteolysis by rather cumbersome ion exchange chromatography [Porter, R. R., Biochem. J. 73:119 (1959)].

While early studies of protease digestion of immunoglobulin G employed soluble papain or pepsin and long incubation times, Putnam et al demonstrated that by increasing the papain to IgG ratio, the time of incubation could be drastically cut down from 16 hours to 1 hour or less [Putnam, W. P. et al, J. Biol. Chem. 237: 717 (1962)]. Difficulties in removal of papain from the cleavage products as well as the possibility of papain contaminating the final $F_{(ab)}$ preparations, become significantly greater with increased protease concentration. Generally, extensive further purification by nonspecific methods such as ion exchange or other chromatographic techniques have heretofore been necessary when elevated protease levels were employed to achieve acceptable reaction rates.

Subsequent to proteolysis, fragments having antigen binding sites [$F_{(ab)}$, $F_{(ab')2}$] and the protease may be separated from fragments having no antigen binding site ($F_c$) and from intact antibody using an immobilized Protein A which specifically binds to the $F_c$ portion of fragmented or intact antibody. The $F_c$ and any undigested IgG may be subsequently eluted from the Protein A column using buffers at acid pH. Removal of the protease has, however, remained a problem.

The development of activated supports has greatly facilitated the preparation of various immobilized proteins and enzymes, including immobilized forms of pepsin and papain which have also been used for the specific fragmentation of antibody. One advantage in using immobilized papain and pepsin is that removal thereof from the reaction mixture may be effected by simple physical separation of the protease subsequent to the digestion of IgG.

A main drawback of this procedure is the slow kinetics of the digestion of IgG by immobilized protease. While the contamination of papain or pepsin could be minimized or eliminated using immobilized protease, the reactions then are in a nonhomogeneous phase, resulting in rates of cleavage which are considerably slower and yields much lower than with systems using homogeneous enzymes. Long incubation times are generally necessary, and incomplete digestion of the immunoglobulin prevents the attainment of adequate yields. It is suspected that limitations on substrate diffusion and steric hindrance inherent in an immobilized enzyme system are probably the major factors causing the reduction in the apparent reaction rate, relative to the kinetics observed with the free enzymes in solution.

It is therefore an object of the present invention to provide methods for fragmentation of immunoglobulins which obviate the problems inherent in the methods heretofore employed for this purpose.

In particular, it is an object of the present invention to provide methods for fragmentation of immunoglobulins, whereby the times required for protease incubation are reduced, the yields of subsequently recovered immunoglobulin fragments are increased, and the separation of IgG and fragments thereof from protease is rapid, simple and effective.

SUMMARY OF THE INVENTION

Pursuant to the present invention, there is provided an improved method for specific fragmentation of immunoglobulins and recovery of the fragments. Through the use of soluble protease (in particular, papain or pepsin) and a complexing agent for the protease, the time required for substantial digestion of immunoglobulins to generate $F_{(ab)}$ and $F_{(ab')2}$ fragments may be reduced to one-third or less than the time heretofore required. Moreover, the yield of immunoglobulin fragments recovered after specific fragmentations of immunoglobulins pursuant to the present invention may be increased by a factor of two or more relative to that achieved using heretofore known methods.

BRIEF DESCRIPTION OF THE DRAWINGS

FIG. 1 illustrates in schematic form various aspects of the inventive method.

DETAILED DESCRIPTION OF THE INVENTION

Figure 2A:
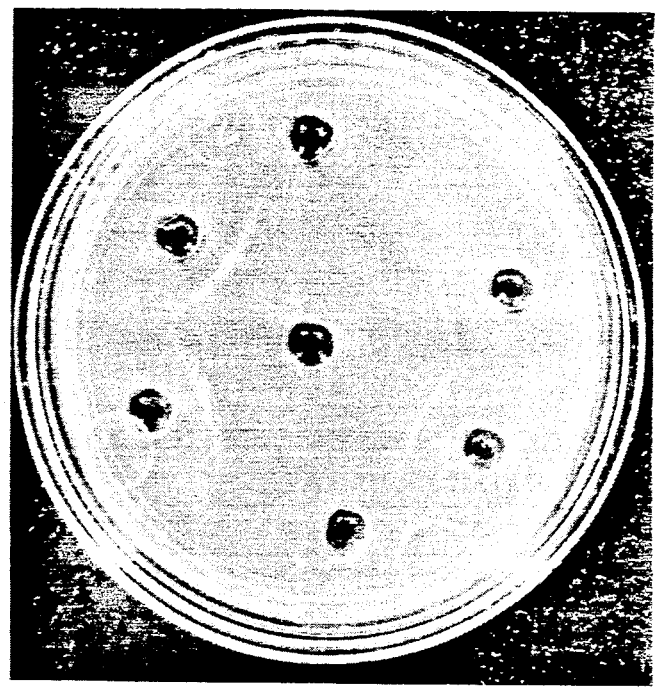
FIGS. 2(a) and (b) illustrate Ouchterlony plates demonstrating the presence of rabbit antibodies to inactivated papain and inactivated pepsin, respectively.

The present invention provides particularly advantageous methods for exploitation of the known high selectivity of certain proteases, in particular papain and pepsin, in digestion of immunoglobulins (most particularly, of the IgG type) to cleave the molecule into $F_{(ab)}$, $F_{(ab')2}$ and $F_c$ fragments. The limitations of the known methods are now overcome in accordance with the present invention, which exploits the advantages of both the free enzyme systems with respect to proteolysis and of immobilized affinity chromatographic techniques with respect to recovery of the final products. As illustrated in FIG. 1, the inventive method utilizes protease (e.g., papain and pepsin) in a soluble form to digest IgG. Complexing agents for the enzymes are then added to complex with the enzymes, thereby facilitating their subsequent removal from solution.

In one embodiment of the invention, rabbit polyclonal antibodies are used to complex with papain or pepsin. This enzyme-antienzyme complex may be subsequently removed from the digestion mixture by binding it to an affinity chromatography agent (for example, Protein A gel). Alternatively, antiprotease IgG may be immobilized using, for example, hydrazide Avidgel AX and the protease removed by adsorbing to this column. Both these methods provide superior yields over shorter periods of time than any of the heretofore known methods.

It has been shown that polyclonal antibodies to papain comprise a spectrum of antibodies, some of which are able to inhibit as much as 92% of papain activity, while others only bind to the enzyme without an inhibitory effect [Arnon, R. et al, Biochemistry 6: 3942 (1967)]. Protease activity of the final immunospecific precipitates reflects the interaction of papain molecules with the range of different species of anti-papain antibodies. It is therefore appropriate to make sure that the anti-protease IgG used to bind the protease itself is not digested; otherwise, the final products might be contaminated with fragments of antiprotease antibodies. Thus, in the preferred process inhibition of protease activity after cleavage of the substrate IgG is appropriate.

Two compounds suitable for use with papain are antipain and leupeptin. Both are able to effectively arrest all of the proteolytic activity, as shown in Table I. Antipain and leupeptin are peptide-based compounds with high affinity for papain and molecular weights around 600 daltons, which could thus easily be dialyzed off, if needed. Complete inhibition of papain activity can be achieved even at 0.05 mg/ml concentrations of the inhibitors.

TABLE I

Inhibition of Papain by Antipain and Leupeptin

| Inhibitor | PAPAIN (0.5 mg) | | PAPAIN (0.5 mg) + IgG (10 mg) | |
|---|---|---|---|---|
| | Inhibition (%) | Time (min.) | Inhibition (%) | Time (min.) |
| ANTIPAIN | | | | |
| 0.4 mg | 100 | 1 | 100 | 1 |
| 0.2 mg | 100 | 1 | — | — |
| 0.1 mg | 100 | 4 | 100 | 4 |
| 0.05 mg | 100 | 15 | 100 | 15 |
| LEUPEPTIN | | | | |
| 0.4 mg | 100 | <1 | 100 | <1 |
| 0.2 mg | 100 | <1 | 100 | <1 |

In the case of pepsin, no inhibitors are necessary; the enzyme is irreversibly inactivated above about pH 6.0, and especially above pH 7.0. By diluting the incubation mixture with a pH 8.5 buffer, it is thus possible to inhibit further proteolysis in pepsin-based systems.

Pursuant to another embodiment of the invention, the high affinity binding between biotin and avidin is exploited as a means to remove the protease from solution. Pursuant to this embodiment of the invention, papain is first biotinylated using an N-hydroxy succinimide ester of biotin. To prevent the inactivation of the enzyme, it is necessary to protect the essential thiol of papain with DTNB prior to biotinylation. The resultant biotinylated papain has comparable activity to that of the native enzyme and the kinetics of cleavage of substrate IgG is similar to that of native papain. The biotinylated papain cleaves the immunoglobulin G to give $F_{(ab)}$ in comparable yield as with native papain, and the protease can also be inactivated by antipain and leupeptin. All of the biotinylated papain can then be captured on an avidin-agarose column.

The rate of pepsin cleavage to IgG to form $F_{(ab')2}$ is slower than the rate of papain cleavage. The time taken to achieve a 70% cleavage of IgG is about 3 hours; to achieve >80% cleavage, up to six hours of incubation with soluble pepsin may be necessary. Under similar conditions at pH 4.5, immobilized pepsin performs extremely poorly, giving only about 30% conversion. The pH optimum for both pepsin and immobilized pepsin is around pH 2.0; however, at pH 4.5 (the pH at which IgG is cleaved), immobilized pepsin has only 3% of the optimal enzyme activity, in contrast to about 20% in the case of free pepsin. The choice of pH 4.5 for the digestion of the IgG is to minimize the effect of low pH on denaturing the immunoglobulins, but the pH effect may contribute to the observed slow rate of cleavage of immobilized pepsin. The use of free pepsin for proteolysis, coupled with subsequent removal of inactivated pepsin either by using an immobilized antipepsin IgG column or by complexing the free pepsin with specific polyclonal antipepsin IgG, leads to very satisfactory products, as judged from the final $F_{(ab')2}$ preparations analyzed using SDS-PAGE gels.

Thus, the use of soluble pepsin and soluble papain to cleave the immunoglobulin molecules has substantial advantages in large-scale preparations of $F_{(ab)}$ and/or $F_{(ab')2}$, both in terms of time and in terms of the increased yields of the final product. The removal of the protease, which might otherwise contaminate the final $F_{(ab)}$ or $F_{(ab')2}$ preparation after digestion of the substrate IgG, is conveniently effected using immobilized anti-protease or soluble anti-protease and immobilized Protein A; in addition, papain can be removed by covalent chromatography using an activated thiol gel. The use of biotinylated papain and its subsequent removal using an avidin-agarose column in accordance with a further embodiment of the invention demonstrates that free enzyme digestion of IgG can be modified in many ways. The use of antipain and leupeptin as inhibitors of papain has the advantage of high specificity and ease of removal of the excess inhibitor (for example, simply by dialysis).

The invention will be better understood by reference to the following example which is intended for purposes of illustration and is not to be construed as in any way limiting the scope of the present invention, which is defined in the claims appended hereto.

EXAMPLE

This example illustrates the various alternative routes provided in accordance with the present invention for using soluble protease in conjunction with a complexing agent. As indicated in FIG. 1, the first step in accordance with all such procedures in treatment of the intact IgG preparation with soluble protease (e.g., papain or pepsin). Pursuant to one process variant, the soluble protease is removed from the reaction mixture using an immobilized form of the corresponding antibody to the protease (e.g., antipapain or antipepsin). In accordance with another alternative, the antibody of the protease is added to the reaction mixture so as to form a protease-/antibody complex, which is subsequently removed using an immobilized protein A gel. In yet another process variant, the protease is inactivated prior to removal thereof from the reaction mixture. In accordance with a further alternative, a soluble biotinylated papain is employed as protease and removed using an avidin-agarose matrix.

Papain, Pepsin, Antipain, Leupeptin, N-benzoyl-L-arginine ethyl ester (BAEE), Haemoglobin, N-ethylmaleimide, human IgG, complete and incomplete Freund's adjuvant were obtained from Sigma Chemical Company (St. Louis, Mo.). AvidChrom Protein A kit, AvidChrom AB Kit, Hydrazide AvidGel, AvidChrom Desalting Cartridges, Hi-Yield TM binding buffer (pH 8.5 buffer), Hi-Yield TM elution buffer (pH 3.5 buffer), immobilized papain and immobilized pepsin were obtained from BioProbe International, Inc. (Tustin, Calif.). Biotin-X-NHS and Avidin-agarose were obtained from Calbiochem (La Jolla, Calif.). Immobilized papain and pepsin were also obtained from Pierce Chemical Co. (Rockford, Ill.).

Papain inactivated with N-ethyl maleimide (NEM) was used as the immunogen for preparation of antipapain. Typically, to a 1 ml suspension of papain (10 mg/ml) in 10 mM sodium phosphate buffer pH 6.5, a 10-fold molar excess of NEM (7.6 mg) was added dropwise and incubated at room temperature for 3 hours. The inactivated papain was dialyzed against phosphate buffered saline pH 7.4 at 4° C. Pepsin used as the immunogen for preparation of antipapain was first inactivated by dialyzing a 10 mg/ml enzyme solution against phosphate buffered saline (pH 7.4).

Rabbits were immunized intra-peritoneally at weekly intervals for six weeks according to the following protocol. First, 1 mg of the antigen in 0.5 phosphate buffered saline emulsified with an equal volume of Freund's complete adjuvant in a Spex Mixer Mill was injected. The second injection was made using a 1:1 emulsion of Freund's incomplete adjuvant and 1 mg of antigen. All subsequent injections comprised 1 mg of antigen in a suspension of alum in phosphate buffered saline. Rabbits were bled after six weeks through the ear veins. When antisera showed good titer, the rabbits were switched to an alternating weekly protocol of boost and bleed cycles using 0.5 mg of antigen.

Antisera were analyzed using Ouchterlony agar diffusion method. Antipapain and antipepsin antisera were further purified using the AvidChrom AB Kit to obtain IgG fractions, according to the manufacturer's recommendations.

Rabbit antibody preparations to papain and pepsin (purified IgG fractions) were coupled to Hydrazide AvidGel AX as follows. 5 mg IgG was oxidized in 0.05M sodium acetate buffer pH 5.0 with 10 mM sodium periodate in the dark for 1 hr at 23° C. ambient temperature. Excess periodate was removed by passing the protein through a desalting cartridge containing 0.05M sodium acetate buffer (pH 5.0). The periodate oxidized IgG was directly coupled to Hydrazide AvidGel AX in 0.05M sodium acetate buffer (pH 5.0) for 12 hours at 4°. The unabsorbed protein was removed by washing sequentially with 1M NaCl and phosphate buffered saline. The ability of the products to bind papain and pepsin was checked using inactivated papain and inactivated pepsin.

Papain was biotinylated using Biotin-X-NHS as follows. First, the active site thiol was protected with 5,5'-dithiobis-2-nitrobenzoic acid (DTNB). A 20 mg/ml solution of papain in 50 mM sodium bicarbonate buffer (pH 8.5) was treated with DTNB at a final concentration of 10 mM and incubated in the dark at 23° C. ambient temperature for 30 minutes. The protein was dialyzed against 50mM sodium bicarbonate (pH 8.5) at 23° C. to remove the excess reagents. Biotin-X-NHS was added at a final concentration of 8 mM (a 20 molar excess) to DTNB-treated papain and incubated at 4° C. for 2 hours. The protein was dialyzed against 0.025M sodium phosphate and 10 mM EDTA (pH 6.2) to remove excess Biotin-X-NHS.

Prior to use, the papain was dialyzed against 0.025M sodium phosphate and 10 mM EDTA (pH 6.2) buffer containing 0.05M cysteine at 4° C. The dialysis was continued with two to three changes of buffer until no more yellow color could be observed in the dialysis buffer.

The ability of biotinylated papain to bind to the avidin-agarose matrix was checked by passing 0.5 mg of biotinylated papain in Hi-Yield TM binding buffer (pH 8.5) through a 1 ml column of avidin-agarose. The column was eluted with a pH 8.5 buffer and the absorbance of the eluting fractions were monitored at 280 nm.

Papain activity was assayed using N-benzoyl-L-arginine ethyl ester in a pH stat and pepsin activity using hemoglobin substrate, according to the procedures given in the Worthington Enzyme Manual.

The ability of antipain and leupeptin to modify papain activity was checked with enzyme, both in the absence and in the presence of immunoglobulin substrate. A 0.5 mg aliquot of active papain was made up in the presence and in the absence of 10 mg of human IgG in 0.025M sodium phosphate buffer containing 10 mM EDTA and 50 mM cysteine (pH 6.2). To each sample, different amounts of either antipain or leupeptin were added and then incubated at 23° C. for 5 minutes. An aliquot of this enzyme was diluted in the same buffer and assayed for papain activity using BAEE as the substrate in the pH stat.

Human or rabbit IgG was used as a representative immunoglobulin to compare the rate of $F_{(ab)}$ generation using either soluble or immobilized papain. Typically, 10 mg of IgG in the papain digestion buffer (0.025M sodium phosphate, 10 mM EDTA, 50 mM cysteine, pH 6.2) was added to either 0.5 ml of activated immobilized papain (0.5 mg equivalent of free papain) or 0.5 mg of activated soluble papain in the digestion buffer. The proteolytic cleavage was carried out for various time intervals at 37° C. At the end of each incubation period, the immobilized papain sample was centrifuged to remove the protease and the supernatant transferred to another tube containing 0.5 ml of pH 8.5 buffer. The gel was washed once with 1 ml of pH 8.5 buffer and supernatants combined. In the case of soluble papain, 0.4 mg of antipain or leupeptin in water was added to inactivate the papain and the mixture diluted with 0.5 ml of pH 8.5 buffer.

The separation of inactivated papain from the rest of mixture was carried by one of two methods. According to one procedure, an excess of anti-papain IgG (3 mg) was added to complex with the inactivated papain and the $F_{ab}$ fragments were separated from the rest of the mixture by passing through a 1 ml protein A cartridge equilibrated with pH 8.5 buffer. This procedure removed both the protease and its antibody in the form of antigen-antibody complexes. The column was eluted with 5 ml of pH 8.5 buffer to collect the $F_{(ab)}$ fragments and the absorbance of the various fractions was read at 280 nm. In an alternative procedure, the reaction mixture was first passed through an immobilized column of antipapain IgG to remove the inactivated papain and then passed through a 1 ml protein A cartridge equilibrated with pH 8.5 buffer. The $F_c$ and the undigested immunoglobulins were eluted from the protein A cartridge with an elution buffer (pH 3.5).

Pepsin fragmentation of human or rabbit IgG was carried out at pH 4.5 in 0.025M acetate (pepsin digestion) buffer using either soluble pepsin or immobilized pepsin. Ten mg of IgG in 1 ml of pH 4.5 pepsin digestion buffer was incubated with either 0.5 mg of soluble pepsin or 0.5 ml of immobilized pepsin (0.5 mg equivalent of soluble pepsin) for various time intervals at 37° C.

Pepsin after incubation with IgG was inactivated by the addition of pH 8.5 buffer, as pepsin is irreversibly inactivated at alkaline pH. Either the digestion mixture was passed through a column of immobilized antipepsin to remove the inactivated enzyme, or an excess of antipepsin IgG was added to complex with the inactivated pepsin. Subsequent separation of the $F_{(ab')2}$ from the rest of the mixture was achieved by using a Protein A column as described in the case of IgG digestion with papain.

Biotinylated papain, prepared as previously described, was activated by dialysis against 0.025M sodium phosphate containing 10 mM EDTA and 50 mM cysteine (pH 6.2). IgG at 10 mg/ml concentration was treated with 0.5 mg of biotinylated papain under conditions similar to those used with soluble papain. After 30 minutes incubation at 37° C., 0.4 mg of antipain was added to inactivate the enzyme and then 0.5 ml of pH 8.5 buffer added to the mixture. The digested mixture was next passed through a 1 ml column of avidin-agarose equilibrated with pH 8.5 buffer to remove the biotinylated papain. The effluent was passed through a protein A column to adsorb the $F_c$ and the undigested IgG. The $F_{(ab)}$ fragments came out unabsorbed from the protein A column. The protein A cartridge was washed with pH 3.5 elution buffer to recover the $F_c$ and undigested IgG fractions. SDS-polyacrylamide gel electrophoresis of proteins were carried out in 10–15% gradient gels in a PHAST System under both reducing and non-reducing conditions according to known methods [Wyckoff, M. et al, Anal. Biochem. 78: 459 (1977)].

Figure 2B:
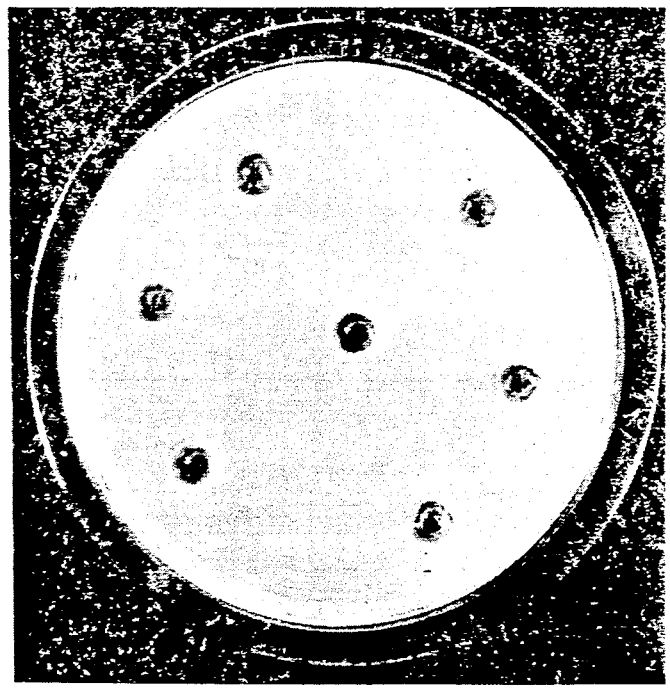

Inactivated pepsin or papain was a potent immunogen for eliciting specific antibodies in rabbits. The presence of specific high titer precipitable antibodies to papain and pepsin is shown in FIGS. 2(a) and 2(b), respectively. The Ouchterlony plates show that the rabbit sera and the purified IgG fractions all gave good precipitin lines. The antisera to papain were found to have higher titer compared to pepsin antibodies.

The immobilization of antipepsin IgG or antipapain IgG on the Hydrazide AvidGel Ax is shown in Table II. The use of site specific immobilization through the carbohydrate moiety in the $F_c$ portion of the IgG molecule has the advantage of increased binding capacity. A loading of 2–4 mg of antiprotease IgG per ml gel was sufficient to bind 0.5 mg of the papain or pepsin. The efficiency of coupling to the hydrazide gel was 67–89% (Table II). No papain or pepsin activity could be detected in the effluent coming out of the immobilized antipapain or antipepsin columns.

TABLE II

Coupling of Antipapain IgG and Antipepsin IgG to Hydrazide Avidgel Ax

| Antibody | IgG Oxidized | Unbound | Bound | Efficiency |
|---|---|---|---|---|
| Antipapain IgG | 2.4 mg | 0.26 mg | 2.14 mg/ml | 89% |
| Antipepsin IgG | 4.1 mg | 1.34 mg | 2.76 mg/ml | 67% |

The esterolytic activity of papain using BAEE as substrate could be effectively inhibited with the peptide-based inhibitors antipain and leupeptin (Table III). At a concentration of 0.05 mg/ml of antipain, 100% inhibition of papain activity was achieved within a short period of 15 minutes. The time taken to achieve complete inhibition decreased with increasing antipain concentration. The presence of 10 mg of human IgG as substrate did not affect the inhibitory activity of either antipain or leupeptin. A concentration of 0.4 mg/ml of leupeptin or 0.4 mg/ml of antipain, which was sufficient to inhibit 100% of papain activity in 1 minute or less, was used as a standard inhibitory concentration for all these studies.

Biotinylation of papain, using Biotin-X-NHS, yielded a protein with 54% of the available free amino groups biotinylated as determined using trinitrobenzene sulfonic acid (Table III). Specific activity of the biotinylated papain after activation with cysteine was comparable to that of the control untreated papain. It was necessary to protect the active site thiol in papain with DTNB prior to biotinylation. Failure to do so resulted in an inactive biotinylated protein. When biotinylated papain (0.5 mg) was passed through a 1 ml Avidin-agarose column, all the protein was held back on the gel, indicating that the level of biotinylation on the papain molecule was sufficient to bind all the protease on the Avidin-agarose column.

TABLE III

Effect of Biotinylation on Papain Activity

| Enzyme | Activity (Unit/mg) | % $F_{ab}$ Generated | % Binding to Avidin-Agarose | Free Amino Groups (μmole/mg) |
|---|---|---|---|---|
| Papain | 7.8 BAEE | 75 | 0 | 1.84 |
| Biotinylated Papain | 7.1 BAEE | 75 | 100 | 0.95 |

Figure 3:
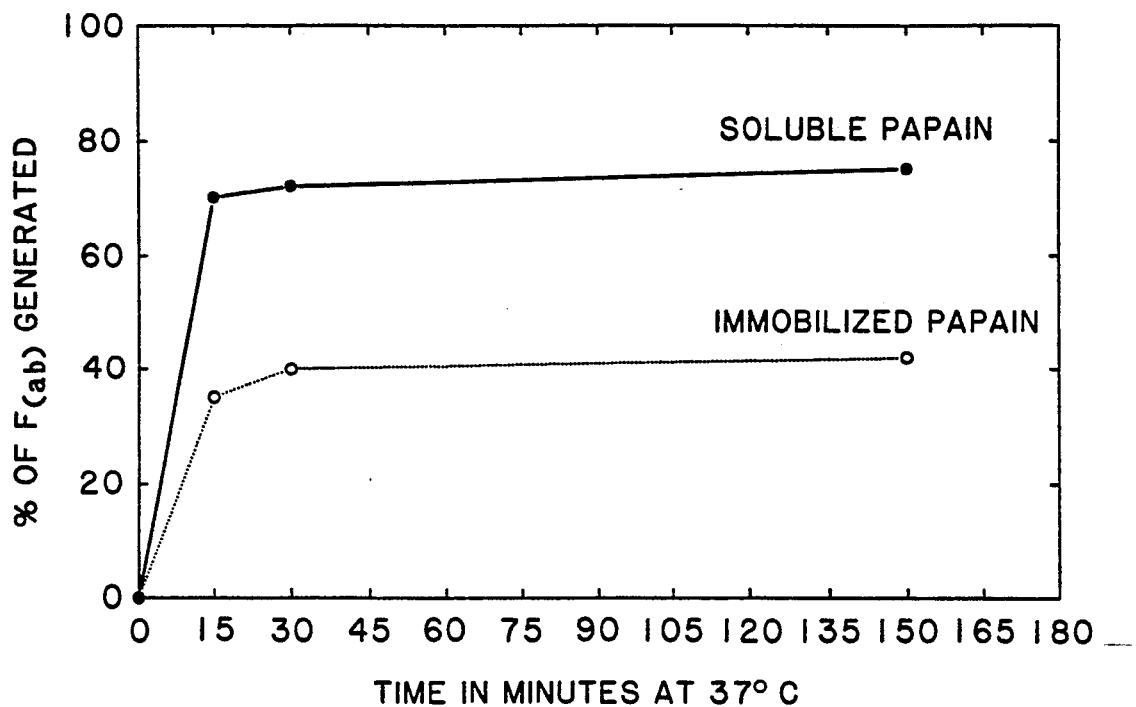
FIG. 3 illustrates the time course of digestion of IgG by soluble and immobilized papain.
Figure 4:
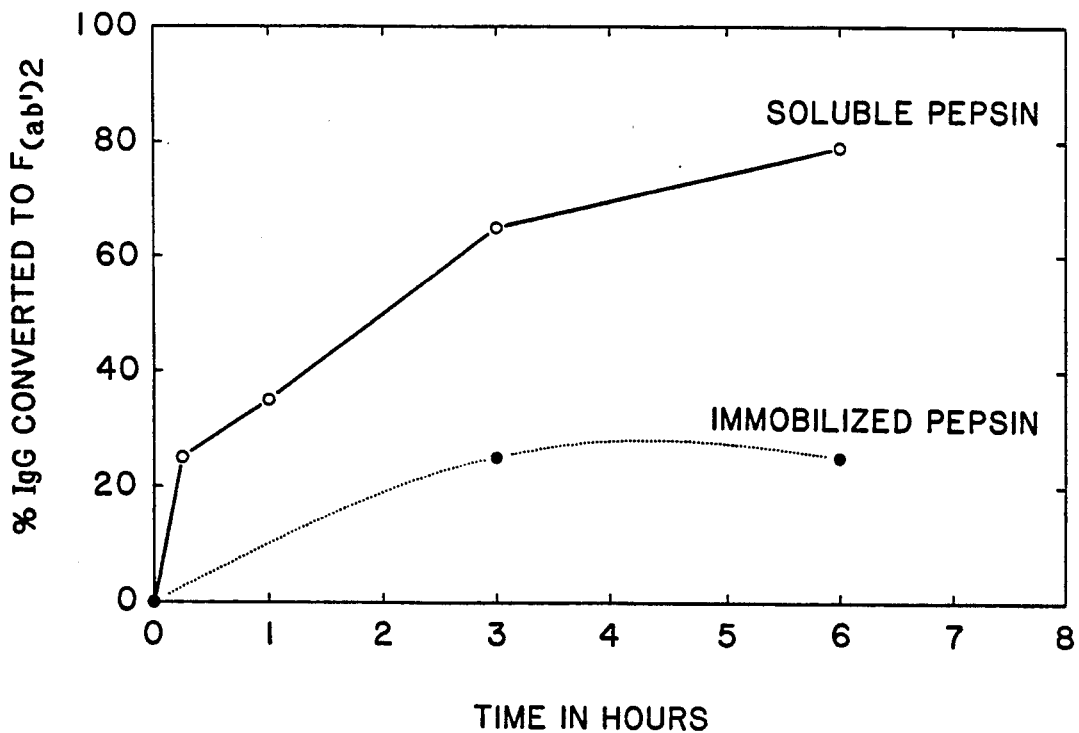
FIG. 4 illustrates the time course of digestion of IgG by soluble and immobilized pepsin.
Figure 5A:
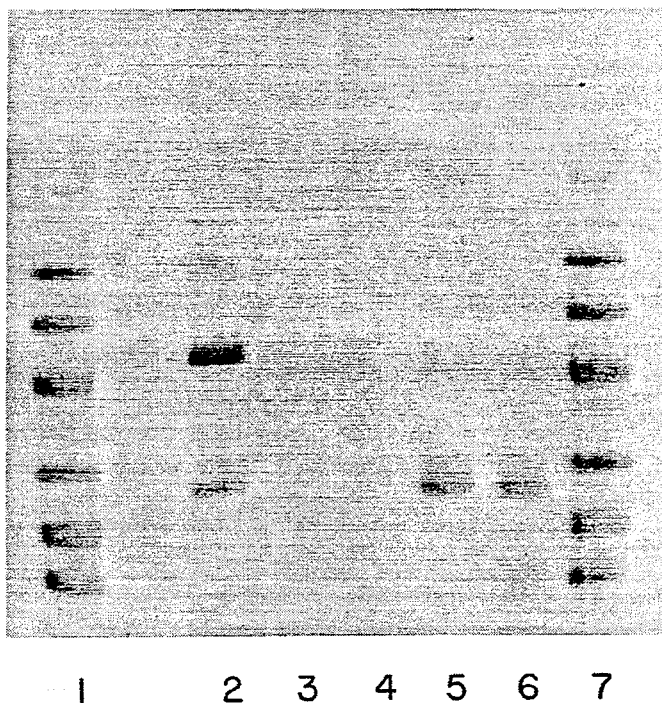
FIGS. 5(a) and (b) illustrate the developed gels for $F_{(ab)}$ and $F_{(ab')2}$ fragments, respectively, after 10–15% gradient SDS-PAGE electrophoresis.
Figure 5B:
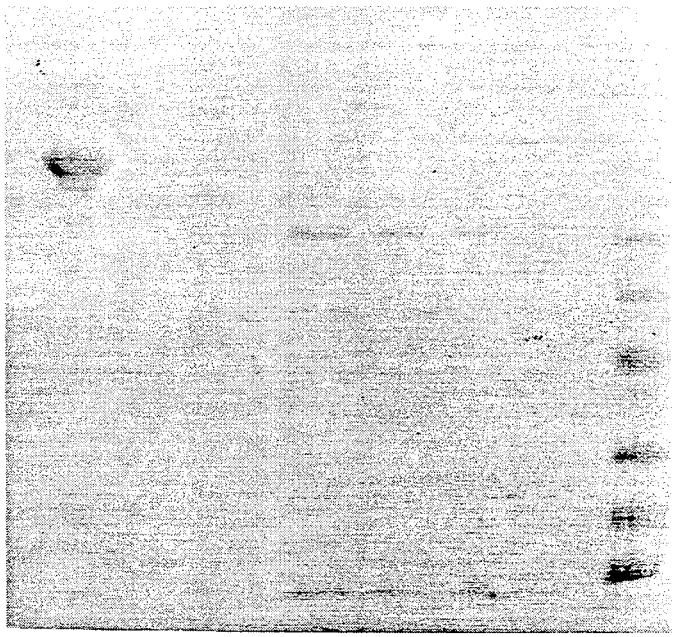

The time course of $F_{(ab)}$ generation from digesting human IgG using the either soluble or immobilized papain is shown in FIG. 3. The Y-axis represents the percentage of IgG digested to $F_{(ab)}$. The rate of digestion of human IgG appears to be biphasic. An initial fast phase (which reaches a maximum in about 30 minutes) was followed by a slower phase, in the case of both the soluble and the immobilized papain. The amount of $F_{(ab)}$ obtained when IgG was digested with soluble papain within the first 30 minutes represented 75% of digestion of the total IgG added, nearly double that obtained using the immobilized form of the enzyme. Increasing the time of incubation with papain up to 2.5 hours only marginally improved the yields. Similar results were obtained when soluble pepsin was compared with immobilized pepsin (FIG. 4). However, the rate of digestion of IgG by either soluble or insoluble pepsin preparations was considerably slower than was the case with either soluble or insoluble papain. Incubation times of up to 6 hours were needed to achieve 80% conversion of IgG to $F_{(ab')2}$ fragments using soluble pepsin; in contrast, only about 25% conversion was achieved over the same 6 hour period using immobilized pepsin. Analysis of the $F_{(ab)}$ and $F_{(ab')2}$ fragments on 10–15% gradient SDS-PAGE gels (FIGS. 5(a) and (b), respectively) both under reducing and nonreducing conditions shows that the fragments are clean and free of contamination as judged by the Coomassie blue stain. In FIG. 5(a), lanes 1 and 7 contain standard molecular weight markers. Lane 2 contains a human IgG standard. Lane 3 contains human IgG digested by soluble papain at 37° C. for 15 minutes. Lane 4 contains human IgG digested by soluble papain at 37° C. for 30 minutes. Lane 5 contains human IgG digested by soluble papain at 37° C. for 60 minutes. Lane 6 contains human IgG digested by soluble papain at 37° C. for 150 minutes. In FIG. 5(b), Lane 1 contains standard molecular weight markers. Lane 2 contains human IgG digested by soluble pepsin at 37° C. for 15 minutes. Lane 3 contains human IgG digested by soluble pepsin at 37° C. for 60 minutes. Lane 4 contains human IgG digested by soluble pepsin at 37° C. for 3 hours. Lane 5 contains human IgG digested by soluble pepsin at 37° C. for 6 hours. In every case, the $F_c$ portion of the digest has been removed by passage through a Protein A column prior to electrophoresis. Thus, the clear advantage of using soluble enzyme systems over the immobilized enzymes for the cleavage of IgG is demonstrated in FIGS. 3 and 4. This advantage is further augmented by the convenience of a combined use of anti-protease and immobilized Protein A.

As the foregoing example illustrates, the inventive method in its various embodiments consistently provided superior results (in terms of yield, reaction time and/or ease of recovery of product) relative to heretofore known methods. According to one route, illustrated, the soluble papain or pepsin was removed from the reaction mixture using the corresponding immobilized antibody (antipapain and antipepsin, respectively). Pursuant to an alternative route, soluble antipapain or antipepsin was used to form a complex with the protease; the protease/antibody complex was then removed using an immobilized protein A gel. In another alternative route, soluble biotinylated papain was removed using an avidin-agarose matrix. In yet another process variant, antipapain or leupeptin was added to inactivate the soluble papain; the inactivated papain was then either removed in the form of a complex with antipapain IgG using an immobilized protein A gel or removed directly using a column of immobilized antipapain IgG. All of these alternative routes have been demonstrated to exploit the advantages inherent in the use of soluble proteases while overcoming the attendant drawbacks in the use thereof.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What we claim is:

1. A method for preparation of immunoglobulin fragments by specific fragmentation of immunoglobulins, comprising:
   treating a solution of said immunoglobulins with a protease soluble in said solution so as to achieve substantially complete fragmentation of said immunoglobulins;
   complexing said protease with a complexing agent to form a protease complex;
   separating said protease complex from said immunoglobulin fragments; and
   inactivating said protease prior to said complexing to ensure that said complexing agent is not digested by said protease;
   wherein said protease is papain and said inactivating is effected by addition of a papain inhibitor.

2. A method for preparation of immunoglobulin fragments by specific fragmentation of immunoglobulins, comprising:
   treating a solution of said immunoglobulins with a protease soluble in said solution so as to achieve substantially complete fragmentation of said immunoglobulins;
   complexing said protease with a complexing agent to form a protease complex;
   separating said protease complex from said immunoglobulin fragments; and
   inactivating said protease prior to said complexing to ensure that said complexing agent is not digested by said protease;
   wherein said protease is papain and said inactivating is effected by addition of antipain or leupeptin.

3. A method for preparation of immunoglobulin fragments by specific fragmentation of immunoglobulins, comprising:
   treating a solution of said immunoglobulins with a protease soluble in said solution so as to achieve substantially complete fragmentation of said immunoglobulins;
   complexing said protease with a complexing agent to form a protease complex; and
   separating said protease complex from said immunoglobulin fragments;
   wherein said protease is biotinylated papain and said complexing agent is avidin.

4. A method for preparation of immunoglobulin fragments by specific fragmentation of immunoglobulins, comprising:
   treating a solution of said immunoglobulins with a protease soluble in said solution so as to achieve substantially complete fragmentation of said immunoglobulins;
   complexing said protease with a complexing agent to form a protease complex; and
   separating said protease complex from said immunoglobulin fragments;
   wherein said protease is biotinylated papain and said complexing agent is avidin and said complexing and said separating are carried out using an avidin-agarose column.

5. A method for preparation of immunoglobulin fragments by specific fragmentation of immunoglobulin, comprising:
   treating a solution of said immunoglobulins with a protease soluble in said solution so as to achieve substantially complete fragmentation of said immunoglobulins;
   complexing said inactivated protease with a complexing agent which forms a protease complex but does not form a complex with fragments of said immunoglobulins;
   said protease having been inactivated prior to said complexing to insure that said complexing agent is not digested by said protease; and
   separating said protease complex from said immunoglobulin fragments.

6. A method according to claim 5, wherein said protease is pepsin and said inactivating comprises adjusting the pH of said solution to above about pH 6.0.

7. A method according to claim 5, wherein $F_c$ fragments are recovered.

8. A method according to claim 5, wherein $F_{(ab)}$ or $F_{(ab')2}$ fragments are recovered.

9. A method according to claim 5, further comprising:
   removing any unfragmented immunoglobulins and $F_c$ fragments from said solution.

10. A method according to claim 5, wherein said removing is carried out using adsorption chromatography.

11. A method according to claim 5, wherein said adsorption chromatography is carried out using immobilized protein A.

* * * * *